(12) United States Patent
Barber et al.

(10) Patent No.: US 7,309,426 B2
(45) Date of Patent: Dec. 18, 2007

(54) COMPOSITION AND METHOD FOR HIGH EFFICIENCY CHROMATOGRAPHY

(75) Inventors: William E. Barber, Landenberg, PA (US); Alan D. Broske, West Chester, PA (US); Timothy James Langlois, Wilmington, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 74 days.

(21) Appl. No.: 10/884,344

(22) Filed: Jul. 1, 2004

(65) Prior Publication Data

US 2005/0236313 A1   Oct. 27, 2005

Related U.S. Application Data

(60) Provisional application No. 60/564,349, filed on Apr. 23, 2004.

(51) Int. Cl.
*B01D 15/08* (2006.01)

(52) U.S. Cl. ............... 210/198.2; 210/502.1; 210/656

(58) Field of Classification Search ........... 210/635, 210/656, 659, 198.2, 502.1
See application file for complete search history.

(56) References Cited

U.S. PATENT DOCUMENTS

| | | | |
|---|---|---|---|
| 3,757,490 A | 9/1973 | Ma | |
| 3,782,075 A | 1/1974 | Kirkland | |
| 3,855,172 A | 12/1974 | Iler et al. | |
| 4,010,242 A | 3/1977 | Iler et al. | |
| 4,017,528 A | 4/1977 | Unger et al. | |
| 4,477,492 A | 10/1984 | Bergna et al. | |
| 4,512,897 A | 4/1985 | Crowder, III et al. | |
| 4,705,725 A | 11/1987 | Glajch et al. | |
| 5,702,610 A | 12/1997 | Hagen et al. | |
| 5,919,368 A | 7/1999 | Quinn et al. | |
| 5,935,442 A * | 8/1999 | Lihme et al. | ............... 210/656 |
| 6,528,167 B2 | 3/2003 | O'Gara | |
| 6,686,035 B2 | 2/2004 | Jiang et al. | |
| 2003/0096113 A1* | 5/2003 | Jacobson et al. | ........... 428/379 |
| 2003/0150811 A1* | 8/2003 | Walter et al. | ............. 210/656 |

OTHER PUBLICATIONS

D. Dewaele et al., Title: "Influence Of The Particle Size Distribution Of The Packing Material In Reversed-Phase High-Performance Liquid Chromatography", Journal Of Chromatography, vol. 260, 1983, pp. 13-21.
Smith et al., Title: "Theoretical Analysis Of The Behavior Of An Heterogeneously Packed Chromatographic Column", Journal Of Chromatography A, Elsevier, Amsterdam, NL, vol. 827, No. 2, Dec. 11, 1998, pp. 241-257.
European Search Report Dated: Aug. 5, 2005.

\* cited by examiner

*Primary Examiner*—Ernest G. Therkorn (57) ABSTRACT

The invention provides novel compositions, columns and methods for improved chromatographic separations. In particular, novel column packings are provided to improve overall chromatographic separation and efficiency. The invention provides a packing material having particles or mixtures of particles that are used for separation of small molecules, proteins or nucleic acids.

7 Claims, 7 Drawing Sheets

Figure 5. Transmittion Electron Micrograph of Silica Particles

FIG. 6

COMPOSITION AND METHOD FOR HIGH EFFICIENCY CHROMATOGRAPHY

Reference to Related Applications

This application claims the benefit of U.S. Provisional Application No. 60/564,349, filed Apr. 23, 2004.

FIELD OF THE INVENTION

The invention relates to compositions and methods for conducting high efficiency liquid chromatographic separations and more specifically, to novel compositions and methods for packing of chromatography columns.

BACKGROUND OF THE INVENTION

Separations using high performance liquid chromatography (HPLC) rely on the fact that a number of component solute molecules in a flowing stream of a fluid percolate through a packed bed of particles, known as the stationary phase. This allows particles to be efficiently separated from one another. Each component has a different affinity for the stationary phase, leading to a different rate of migration and exit time for each component from the column. The separation efficiency is determined by the amount of spreading of the solute band as it traverses the column.

Plate theory is commonly used to describe the passage of a solute through a chromatographic column and the band broadening. Plate theory explains band broadening in terms of a number of rate factors. For instance, separations may be considered to be made in a plurality of connected, equal, discrete, hypothetical steps, each volume of which contains both stationary and moving phases and in each of which complete equilibrium is established. Each such stage is called a "theoretical" plate. In such cases the number of theoretical plates in the column is calculated from the degree of separation. The length of the column is important to this calculation in relation to the theoretical plates. The length of the column per calculated theoretical plate is called the "height equivalent to a theoretical plate" or H, and is a measure of the phenomenon of band broadening.

Band broadening is important to separations and is indicative of the quality of the separation. For instance, generally speaking the broader the bands in the separation the worse the separation or column efficiency.

Separations are also based on the relationship between the phases. In chromatography, one phase is stationary and the other phase is mobile. The mobile phase moves past the stationary phase at a relatively fast rate so that complete equilibrium is, in fact, not attained between the two phases. This must be considered when performing separations to avoid peak broadening and to obtain clean and efficient separations.

In applying plate theory to chromatographic columns, all of the solute is assumed to be present initially in the first plate volume of the column. Dispersion is based on the distribution coefficient. In this instance, the distribution coefficient is constant for the solute concentrations encountered, and the solute rapidly distributes itself between the two phases in each plate volume.

Columns that provide minimum peak broadening are indicative of clean separations and are desirable for HPLC systems and processes. The nature of the packing put into the column and manner in which the column is packed, are all of high importance in getting clean and effective separations of sample components. It is, therefore, desirable to minimize the various processes that determine relative band broadening with deleterious effects on column performance. The effect of each of these processes on the column plate height H can be related by rate theory to such experimental variables as mobile-phase velocity u, packing particle diameter $d_p$, and the solute diffusion coefficient in the mobile phase. The major band broadening processes in HPLC contributing to height equivalent to a theoretical plate, H, are generally considered by the Van Deemter equation. In addition, this equation can be simplified to relate the three important variables of particle size, fluid velocity and diffusion coefficient. In this reduced equation, as the particle size increases the efficiency should decrease. As the fluid velocity increases, the equation predicts that the mass transfer term will dominate the efficiency with a deterioration proportional to the product of the velocity and particle diameter. It will be appreciated that minimization of band broadening is desirable to insure that one obtains optimum separation of solutes, in analytical chromatography, product purity, and preparative chromatography.

However, the advantages obtained from smaller particles in terms of column efficiency must be offset by the disadvantages of higher back pressure, which include increased instrument cost and reduced reliability caused by the higher system stresses. Furthermore, it is normally asserted that ideally, particles used in liquid chromatography columns should be monodisperse, and have as narrow a particle size distribution as possible. For example, Dewaele and Verzele disclose (J. Chromatography, 260 (1983) 13-21) that blends of irregular shaped materials with different particle sizes yield packing with greater pressure than the corresponding equivalent mean particle size. The work by Dewaele and Verzele was restricted to two component blends. Each component of the blends having a monodisperse particle distribution and a mean for the distribution. In addition, the means of the particle size distributions differed from each other by greater than 40%. In other words, blends of particles that differed greatly in mean diameter where ineffective in lowering overall back pressure of the system.

It, therefore, would be desirable to provide a novel material or materials that would allow for efficient and effective separations, yet avoid the problem of increased back pressure and poor separations and efficiency.

SUMMARY OF THE INVENTION

The invention provides an apparatus, method and packing composition for chromatography. The packing composition comprises two or more components that possess a particle size distribution (PSD) and a mean for the particle size distribution. The difference between any two means of the particle size distributions being less than 40% of the mean of the larger component.

Alternatively, the difference between the diameters at the two peaks of the distribution is less than or equal to 40% of the value of the average of the diameters at the two peaks.

The particles can be of any inorganic or hybrid inorganic/organic material that is suitable for chromatographic use.

The invention also provides chromatography columns and packings that comprise particles with a PSD that is broadened relative to packings that have higher back pressures.

The invention also provides a method of making and using the particles or packings to separate various organic and inorganic materials.

Lastly, the invention provides particle dimmers that may be useful in overall separations and increased efficiency.

DETAILED DESCRIPTION OF THE INVENTION

Before describing the invention in detail, it must be noted that, as used in this specification and the appended claims, the singular forms "a," "an," and "the" include plural referents unless the context clearly dictates otherwise. Thus, for example, reference to "a material" includes combinations of materials, reference to "a compound" includes admixtures of compounds, reference to "a nitride" includes a plurality of nitrides, and the like.

In describing and claiming the present invention, the following terminology will be used in accordance with the definitions set out below.

The term "essentially" when used herein to denote a physical property means within 10% of the stated value.

The term "packing material" refers to a non porous, porous, or mixtures of porous, non-porous or superficially porous packing materials. The term is not intended to be limiting and includes combinations and blends of the above mentioned materials.

The term "stationary phase" refers to a phase that comprises particles that comprise an organic or an inorganic material that optionally has an organic moiety bonded to it that renders the surface of the particle useful in certain chromatographic separations. In certain instances, these particles or materials are fixed in a column and do not move. Examples of inorganic materials are, but are not limited to, silica, zirconium and titanium oxides. An example of an organic material is styrene divinyl benzene copolymer. An inorganic material can also include what are known in the art as "hybrid" particles that contain organic and inorganic moieties in the same structure, and are described in U.S. Pat. No. 4,017,528, assigned to Merck, and U.S. Pat. Nos. 6,528,167 and 6,686,035 assigned to Waters and all three incorporated herein by reference.

The invention is described herein with reference to the figures. The figures are not to scale, and in particular, certain dimensions may be exaggerated for clarity of presentation.

EXAMPLE 1

Two samples of bonded silica particles were prepared by standard methods known to those skilled in the art, and described, for example in U.S. Pat. Nos. 3,782,075, 3,855,172 and 4,010,242 all assigned to Du Pont and all three incorporated herein by reference. Particles were bonded using the bonding chemistry described in U.S. Pat. No. 4,705,725, also to Du Pont and also incorporated herein by reference. The bonded phase was a C-18 (octadecyl) material. It should be noted that these processing techniques produce a defined particle size distribution (PSD). This is a common and well known in the industry standards. It should be noted although the present invention is described in the context of these methods, the invention should not be construed to be limited to components with particle size distributions. For instance, techniques could be used or developed that produce nearly identical or similar size particles that are not in a distribution. The invention is applicable also to these types of materials and contexts.

Figure 1:
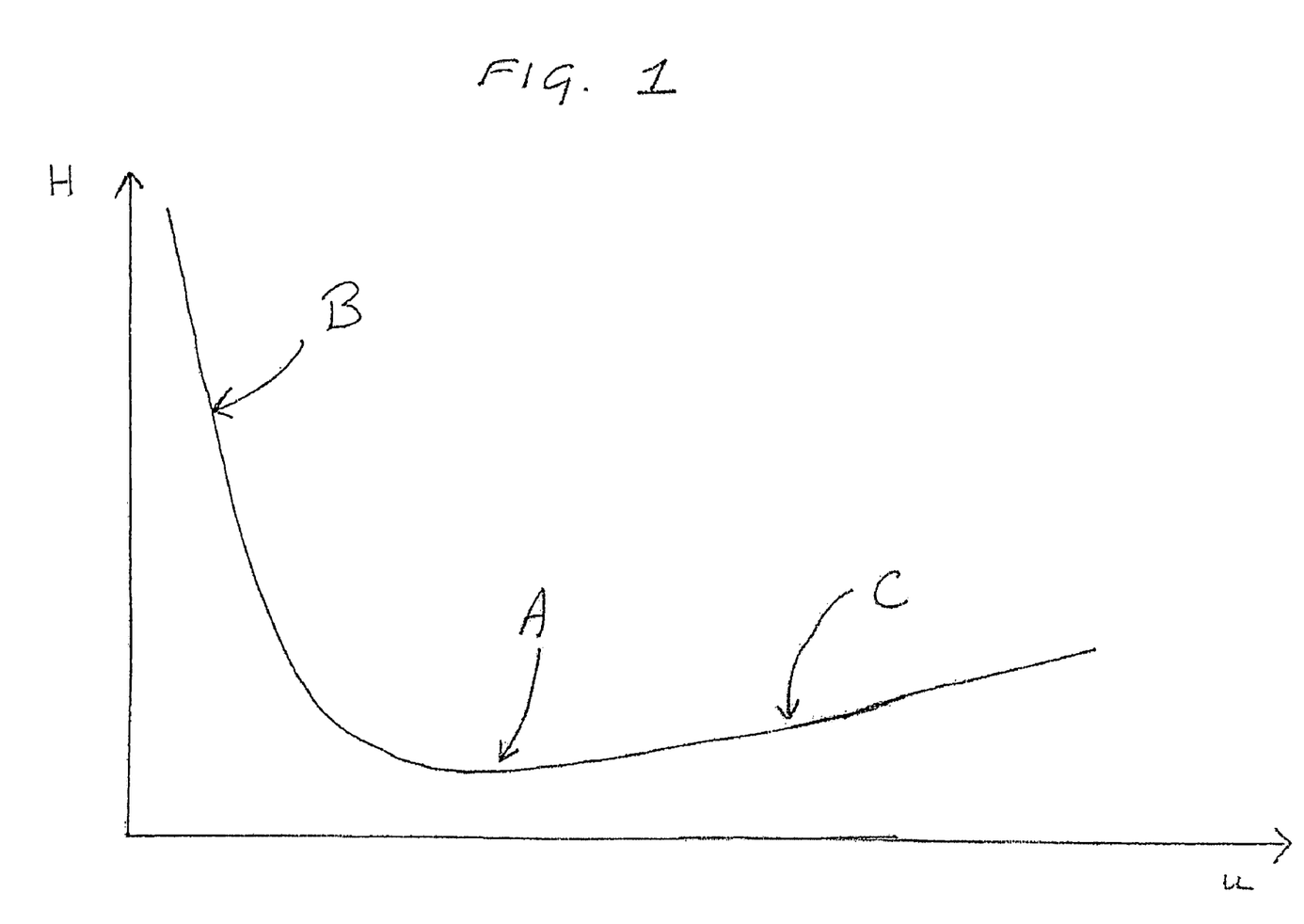
FIG. 1 shows an example of a van Deemter plot of plate height vs. linear velocity of mobile phase for an HPLC system.
Figure 2:
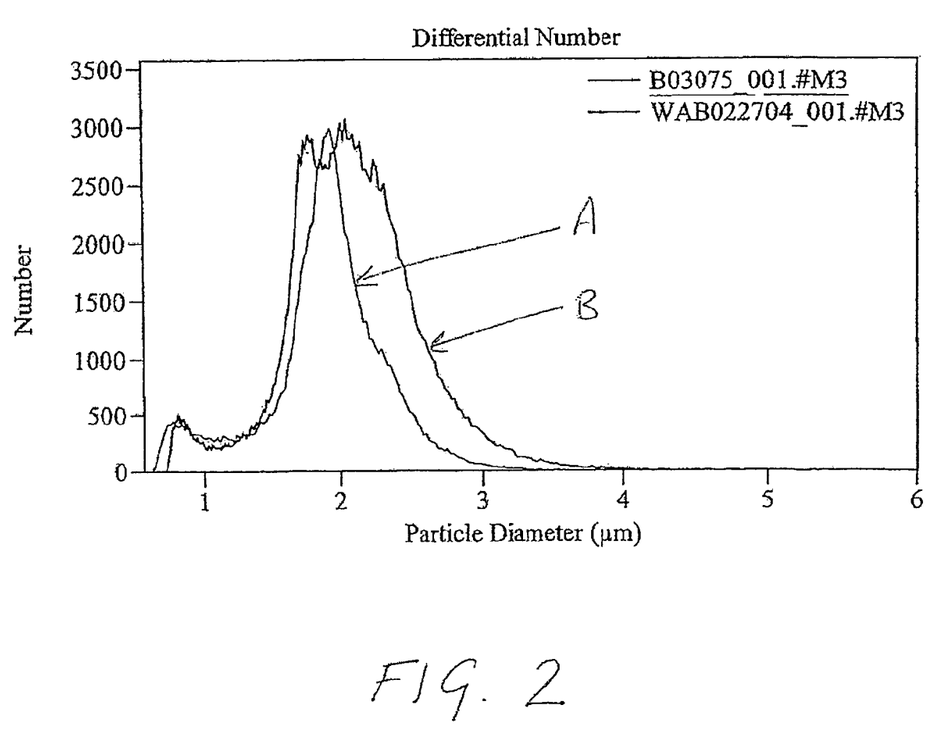
FIG. 2 shows particle size distribution plots overlaid on each other of a monodisperse and a bidisperse sample.

FIG. 2 shows particle size distributions obtained by Coulter counter (Beckman Instruments, Hialeah, Fla.) on both samples. Number of particles per bin were counted with 256 bins from below 1 um to 6 um. As can be seen from FIG. 2, one sample (labeled A) was monodisperse, and one peak can be seen at approximately 2 μm. The second sample provides two peaks and was essentially a blend of particles of 1.8 um and 2.2 um in diameter, as measured on the Coulter counter.

The two samples were packed using standard techniques into HPLC columns of diameter 4.6 mm and length 30 mm. HPLC experiments were conducted on an Agilent 1100 instrument (Agilent Technologies, Wilmington, Del.) to measure back pressure as a function of volumetric flow rate of mobile phase through the columns and reduced plate height as a function of linear flow rate. The eluent was 85:15 acetonitrile:water (volumetric ratio) at a temperature of 20° C. The sample was octanophenone, with UV detection at 245 nm.

Figure 3:
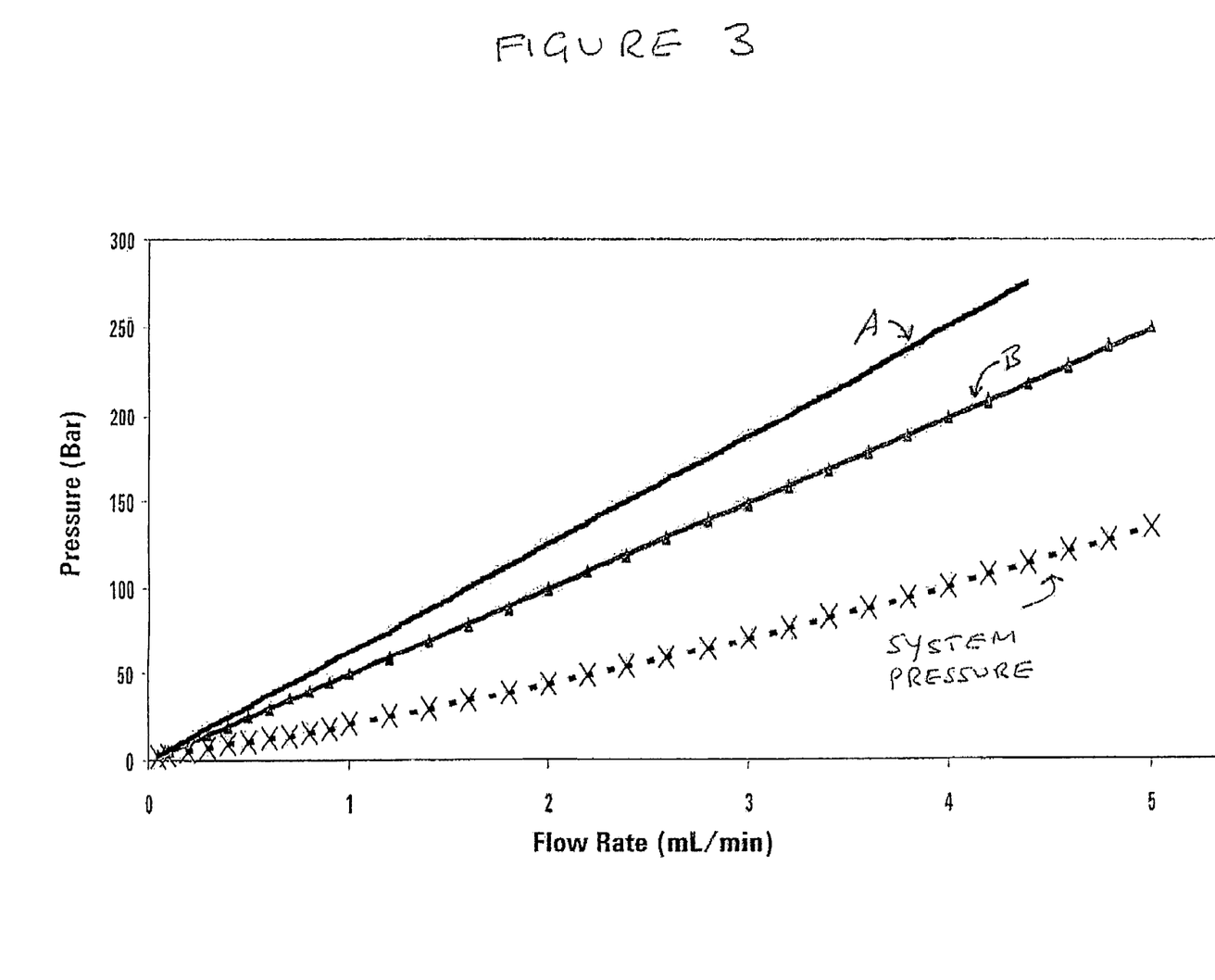
FIG. 3 shows a plot of back pressure against flow rate for HPLC experiments that compare the particles with the size distributions shown in FIG. 2.

In FIG. 3 is shown back pressure plots from the HPLC experiment. Samples A and B are shown and sample B shows a lower back pressure by 20% at the optimum flow rate as judged by the van Deemter plot in FIG. 4 than sample A.

Figure 4:
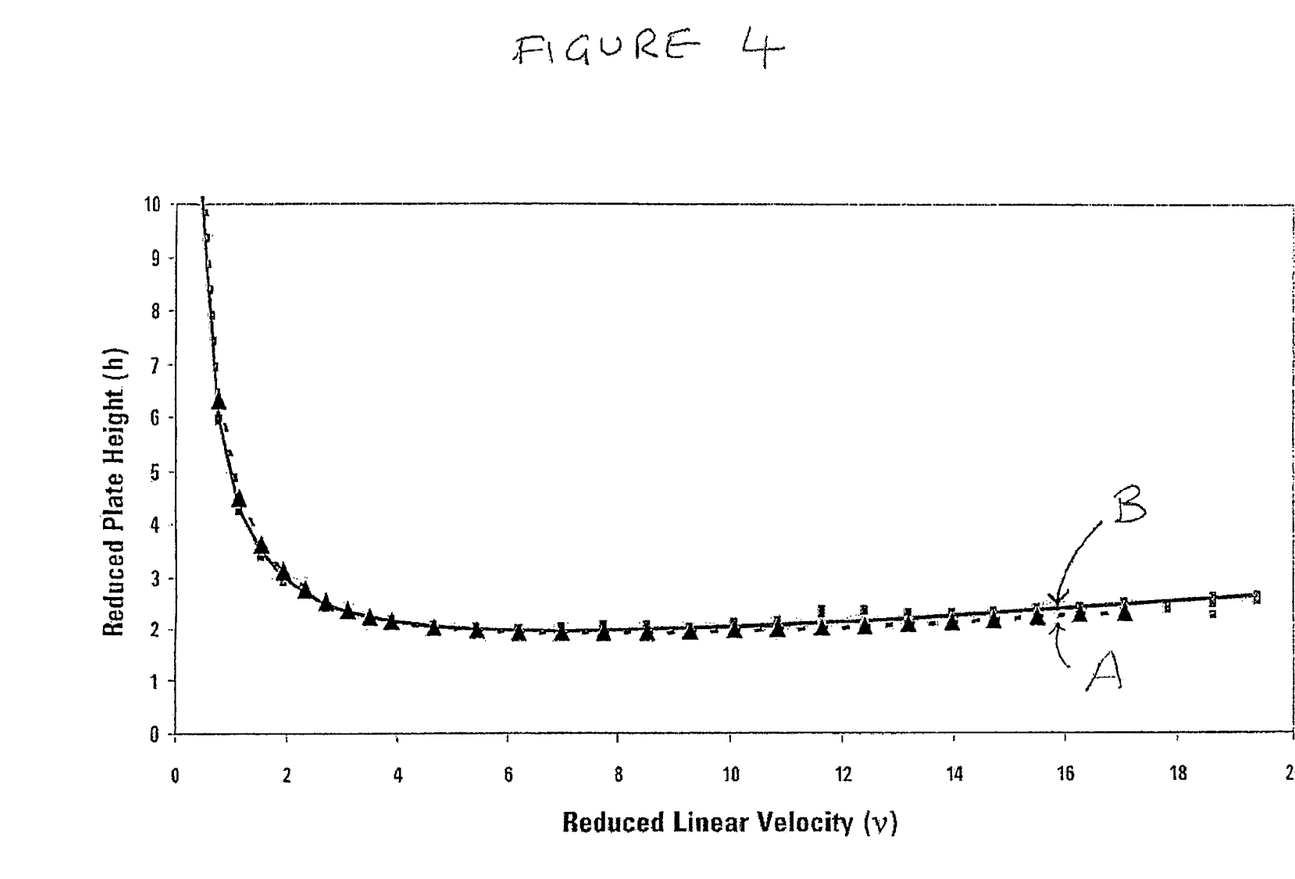
FIG. 4 shows a van Deemter plot of the experiments shown in FIG. 3.

In FIG. 4 is shown the van Deemter curves for the sample columns. Reduced plate height was calculated using the same mean particle size for both columns. The optimum flow rates in terms of maximum column efficiency are judged by the position of the minimum in the plots, and as can be seen from the figure, around the minimum plate height the plate heights differ by no more than a few percent (0.00385 mm for the sample B vs. 0.00372 mm for sample A) and the minima in the curves are broad enough that the performance of the columns is essentially identical over the working velocity range of the columns.

The broader particle size distribution of sample B has, therefore, proved effective in significantly reducing back pressure in the HPLC experiment without sacrificing significant column efficiency.

Figure 5:
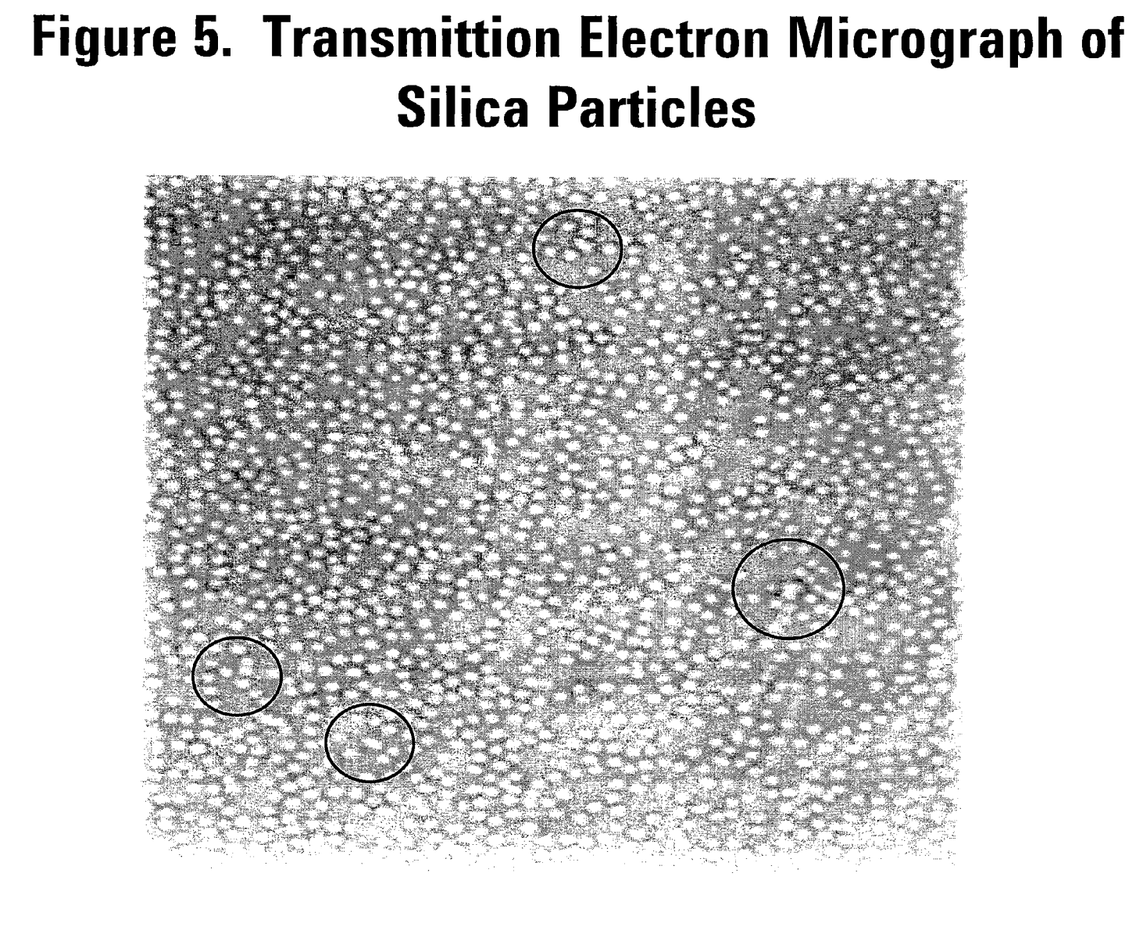
FIG. 5 shows transmission electron micrographs of particles of the invention.

In FIG. 5 is shown a transmission electron micrograph (TEM) at a magnification of 500× of a slide that holds particles with the broad PSD as described above. Although it is generally not possible to correlate Coulter counter data with TEM data, a number of the particles in the micrograph appear to be joined as dimers. Without wishing to be constrained by mechanism, it may, therefore, be possible that some or all of the bimodal character of the PSD's as measured by the Coulter counter is caused by dimeric structures. The scope of the invention claimed herein includes PSD's in which dimeric particle structures exist.

EXAMPLE 2

HPLC columns with the same bonded phase of example 1 and of internal diameter 4.6 mm and length 30 mm were prepared. The columns were loaded with blends of particles with unimodal particle size distributions of 1.8u mean diameter and 3.5μ. Conditions of the HPLC experiment were;

| Instrument: | Agilent 1100 (Agilent Technologies, Wilmington, DE). |
| --- | --- |
| Injection Volume: | 2 ul |
| Detection: | 254 nm UV with a 1.8 ul cell |
| Mobile phase: | 60/40 methanol/water |
| Flow rate: | 1.5 ml/min |
| Temperature: | Room temperature |
| Sample: | Uracil, Phenol, 4-chloronitrobenzene, and toluene. |

The results of the HPLC experiment are shown in table 1.

TABLE 1

| Percent 3.5 μm particles by weight in blend | Efficiency (plates) | Pressure (bar) |
| --- | --- | --- |
| 0 | 7500 | 377 |
| 10 | 7200 | 357 |
| 20 | 7200 | 333 |
| 25 | 7200 | 330 |
| 30 | 7100 | 320 |
| 40 | 6900 | 316 |
| 50 | 5900 | 299 |

Figure 6:
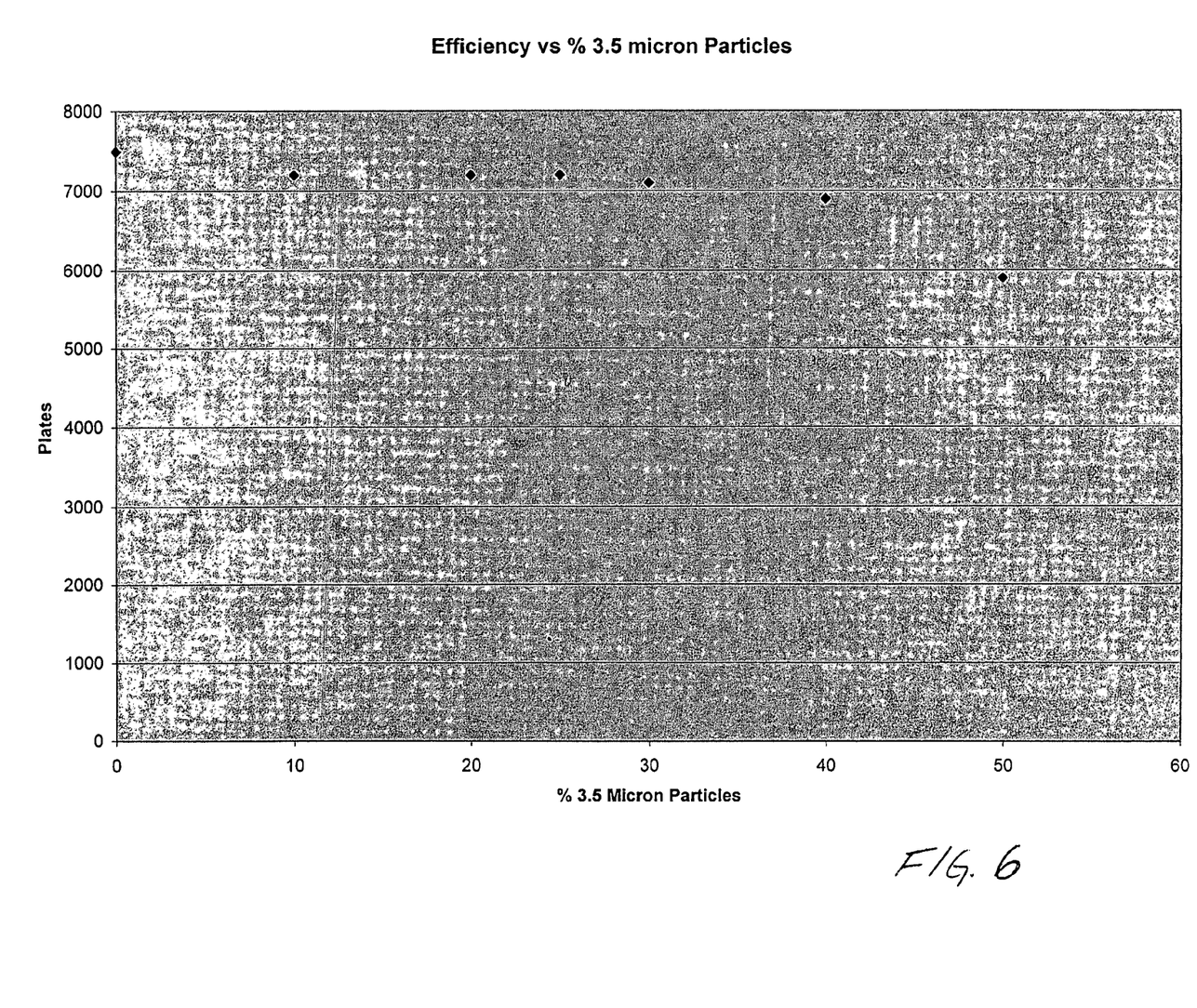
FIG. 6 shows a pilot of efficiency vs. % of large particles for an HPLC experiment in which the column packing is a blend of large and small particles.
Figure 7:
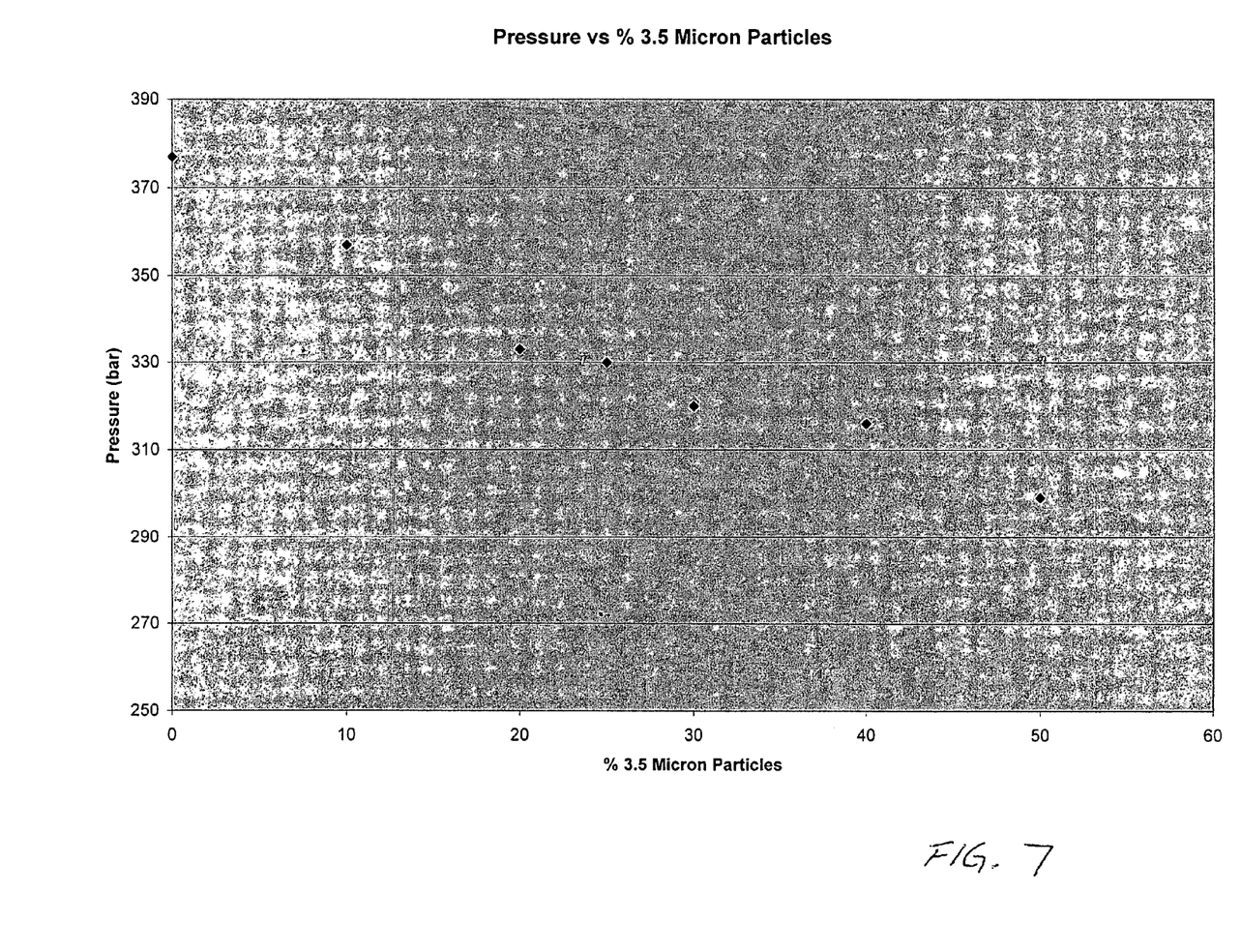
FIG. 7 shows a plot of system pressure vs. % of large particles for the same experiment as in FIG. 6.

From m table 1 can be seen that the efficiency advantage of the smaller, 1.8 μm is substantially retained with the addition of up to 30% of the larger particles, with a saving in system pressure of 57 bar. FIGS. 6 and 7 show this effect more clearly, where the efficiency vs. % 3.5 μm plot shows a plateau up to a 40% particle inclusion and the pressure vs % 3.5 μm particle plot is essentially linear.

From the discussion in the section "background of the invention" it is not immediately clear why such a blend of particle sizes should be able to demonstrate such high efficiencies relative to the back pressure required to operate the column. Without wishing to be constrained by mechanism, possible contributions to the effectiveness of the column may come from increased ease of packing the column, leading to chromatographic efficiencies that are closer to the theoretical maximum of the smaller particle. Another possible contribution may come from boundary packing effects between the stationary phase and the wall of the column into which the stationary phase has been packed.

Although the examples given above are limited to a particular particle size distribution and set of chromatographic conditions, the invention is in no way to be construed as limited to these conditions. For example it will be apparent to one skilled in the art from this disclosure that the column packing can comprise other materials other than bonded silica and still retain the same advantages due to the PSD as with the silica column.

In addition, the PSD need not be bimodal, as long as it is broad enough to provide the required decrease in back pressure compared to a narrow PSD with the same mean particle size. One skilled in the art would be able, without undue experimentation, to develop particles with PSD's that demonstrate optimized back pressure and efficiency relationships.

The particles in the stationary phase need not all be porous to the same degree. For example the stationary phase can comprise a blend of particles that are porous to different degrees, for example particles that are non porous or particles that are superficially porous. An example of superficially porous particles is given in U.S. Pat. No. 4,477,492 assigned to Du Pont and incorporated herein by reference. In summary, any blend of particles of differing porosity in sizes that provide a reduction in back pressure relative to a stationary phase of essentially the same efficiency, is covered by the scope of the invention.

The mean particle size of the particles of the invention is also not be construed as limited by the example described above. The mean particle size is only limited by the usefulness of the particles as a chromatographic stationary phase and typically will be in the range 0.5μ to 100μ and 1μ to 10μ. Although the examples given above relate to use of the particles in analytical applications, the advantages of the invention for use in preparatory chromatography, where higher efficiencies can be obtained for a given back pressure, will be apparent.

Although the examples show application of the invention to small organic molecule (uracil, phenol, toluene, and 4-nitrobenzene) the invention also applies to use for separation of large polymers, proteins, nucleic acids and peptides. Other biological molecules known in the art may also be separated using the present invention.

We claim:

1. A composition of matter for use as a stationary phase in a chromatography packing material, said packing material comprising particles or mixtures of different porosity particles that have a bimodal number average particle size distribution in which the difference between the diameters at the two peaks of the distribution is less than or equal to 35% of the value of the average of the diameters at the two peaks and is effective in significantly reducing back pressure in HPLC without sacrificing significant column efficiency.

2. A composition as recited in claim 1, wherein the stationary phase comprises a material selected from the group consisting of organic materials, inorganic materials, hybrid materials, and combinations thereof.

3. A composition as recited in claim 2, wherein the packing material comprises particles that are spherical and particles that are composite bonded structures that are dimers of the spherical particles.

4. A composition as recited in claim 1, wherein the composition is suitable for use in liquid chromatography separations.

5. A composition as recited in claim 4, wherein the composition may be used in preparative separations.

6. A composition as recited in claim 1, wherein the composition is suitable for use in gas chromatography separations.

7. A composition as recited in claim 1, wherein the packing material comprises dimers.

* * * * *

UNITED STATES PATENT AND TRADEMARK OFFICE
CERTIFICATE OF CORRECTION

| | |
|---|---|
| PATENT NO. | : 7,309,426 B2 |
| APPLICATION NO. | : 10/884344 |
| DATED | : December 18, 2007 |
| INVENTOR(S) | : Barber et al. |

Page 1 of 1

It is certified that error appears in the above-identified patent and that said Letters Patent is hereby corrected as shown below:

On the title page, in item (75), in "Inventors", in column 1, lines 2-3, delete "West Chester, PA" and insert -- Wilmington, DE --, therefor.

Signed and Sealed this

Fifteenth Day of July, 2008

JON W. DUDAS
*Director of the United States Patent and Trademark Office*